United States Patent [19]

Kimura et al.

[11] Patent Number: 5,449,750
[45] Date of Patent: Sep. 12, 1995

[54] PROLYL ENDOPEPTIDASE INHIBITORS SNA-115 AND SNA-115T, AND PROCESS FOR THE PRODUCTION AND PRODUCTIVE STRAIN THEREOF

[75] Inventors: Kenichi Kimura; Fumiko Kanou; Hidetoshi Takahashi; Kazuhiko Kurosawa; Makoto Yoshihama, all of Tochigi, Japan

[73] Assignee: Snow Brand Milk Products Co., Ltd., Hokkaido, Japan

[21] Appl. No.: 977,444

[22] PCT Filed: Jun. 19, 1992

[86] PCT No.: PCT/JP92/00784

§ 371 Date: Feb. 17, 1993

§ 102(e) Date: Feb. 17, 1993

[87] PCT Pub. No.: WO93/00361

PCT Pub. Date: Jul. 1, 1993

[30] Foreign Application Priority Data

Jun. 20, 1991 [JP] Japan .................................. 3-176228
Feb. 28, 1992 [JP] Japan .................................. 4-078262

[51] Int. Cl.⁶ .......................... C07K 7/64; C07K 7/08; A61K 38/12

[52] U.S. Cl. ....................... 530/321; 530/317; 530/326; 530/300; 514/9; 514/13; 514/11; 514/2; 435/71.1; 435/71.3

[58] Field of Search ............... 530/317, 321, 326, 300; 514/9, 13, 11, 2; 435/71.1, 71.3

[56] References Cited

U.S. PATENT DOCUMENTS

4,999,349 3/1991 Toda et al. .......................... 530/317

OTHER PUBLICATIONS

The Merck Manual of Diagnosis & Therapy, 11th edition, (1966), pp. 1161–1163.

*Primary Examiner*—Jill Warden
*Assistant Examiner*—T. D. Wessendorf
*Attorney, Agent, or Firm*—Burgess, Ryan & Wayne

[57] ABSTRACT

Prolyl endopeptidase inhibiting compounds SNA-115 and SNA-115T are provided having molecular formulas of $C_{113}H_{142}N_{26}O_{27}$ and $C_{113}H_{144}N_{26}O_{28}$ respectively. SNA-115T has the following structural formula:

Arg Tyr Asp Trp Trp Pro Tyr Gly Asp Leu Phe Gly Gly His Thr Phe Ile Ser Pro

Processes are also provided for the production of SNA-11 by culturing the SNA productive microorganism and production of SNA-115T by degradation of SNA-115 with trypsin. Both SNA-115 and SNA-115T exhibit prolyl endopeptidase inhibitory properties.

2 Claims, 10 Drawing Sheets

SEQUENCE LISTING ( 1 ) GENERAL INFORMATION:

( i i i ) NUMBER OF SEQUENCES:1

( 2 ) INFORMATION FOR SEQ ID NO:1:

( i ) SEQUENCE CHARACTERISTICS:
( A ) LENGTH:19
( B ) TYPE:AMINO ACID
( D ) TOPOLOGY:CYCLIC or LINEAR ( i i ) SEQUENCE DESCRIPTION:SEQ ID NO:1:

Arg Tyr Asp Trp Trp Pro Tyr Gly Asp Leu Phe Gly Gly His Thr
                  5                   10                  15

Phe Ile Ser Pro

PROLYL ENDOPEPTIDASE INHIBITORS SNA-115 AND SNA-115T, AND PROCESS FOR THE PRODUCTION AND PRODUCTIVE STRAIN THEREOF

FIELD OF THE INVENTION

This invention relates to novel prolyl endopeptidase inhibitors SNA-115 and SNA-115T, and their productive novel microorganism and a process for their production.

The prolyl endopeptidase inhibitors SNA-115 and SNA-115T of the present invention are useful for the effective component of anti-amnestic agents, or preventive and treatment agents against acquired immunodeficiency syndrome (AIDS) and anti-HIV diseases.

BACKGROUND OF THE INVENTION

Average actuarial rate has been extending with the progress of medical sciences and technology, and senile dementia is now becoming a serious problem not only for family members including the patient but also for social structure. The existing drugs have been effective only for complicated symptoms and related diseases of senile dementia, and new drugs effective for the essential pathology are required.

Prolyl endopeptidase (EC 3.4.21.25) is an enzyme that selectively cleaves the carboxyl site of proline in peptides containing proline both in vitro and in vivo conditions, and degrades and inactivates neural peptide, vasopressin which is presumed to participate in mnemonic function [Nippon Nōgeikagaku Kaishi, 58, 1147–1154 (1984)]. Thus the prolyl endopeptidase inhibitor is expected to exhibit anti-dementia activity and a variety of synthetic inhibitors have been reported to exhibit anti-amnestic effects in experimental studies in rats and mice [J. Pharmacobio-Dyn., 10, 730–735 (1987)]. Recently, a relationship between Alzheimer's disease type dementia and prolyl endopeptidase has attracted attention and a significant elevation of the enzyme level in the brain of patients [Experientia, 46, 94–97 (1990)], relationship to the C-terminal cleavage of A4($\beta$)-amyloid protein [FEBS LETTERS, 260, 131–134 (1990)] and effect of substance P which can be degraded by prolyl endopeptidase on the nerve degeneration caused by $\beta$-protein [Proc. Natl. Acad. Sci., 88, 7248–7251 (1991)] have been reported. These findings intensified the expectation to prolyl endopeptidase inhibitor as an anti-amnestic agent. Particularly, the majority of existing synthetic drugs having similar chemical structures elucidated the structure-activity relationship in the inhibitors [Agric. Biol. Chem., 55, 37–43 (1991)]. Their activity, absorption, excretion and stability within living body have been established. On the other hand, inhibitors obtained from natural resources such as cultured Actinomycetes are expected to have unique and different structures from those of synthetic compounds, and advantages in the inhibitory activity, absorption, excretion and stability are awaited.

Furthermore, an emergent and definitive treatment of AIDS is required. There is no established treatment despite its high mortality rate and many countries including United States are concerned over serious social problems. At present, azidothymidine (AZT) has been used, but it also has potent adverse effects such as suppression of bone marrow, and drugs with a more direct action and less toxicity are desired. A recent experiment using a synthetic prolyl endopeptidase inhibitor found a particular relationship between the inhibitory activity of prolyl endopeptidase and an inhibitory activity on syncytium formation which is characteristic of the intercellular infection of HIV. Thus a new route for the development of new antiviral drugs based on the new mechanisms is expected [Japan Unexamined Patent Publication No. 124818 (1990)].

DISCLOSURE OF THE INVENTION

The present invention is derived from the background shown above and the inventors searched a prolyl endopeptidase inhibitor from natural resources using microbial fermentation products. A microorganism productive of the inhibitor was found and the product was identified and confirmed as a new compound. Furthermore, the new microorganism was comparatively investigated with similar known microorganisms belonging to the same genus to determine whether they produce the same compound or not and it was found that the particular known microorganisms are productive of the new compound. Additionally, an industrial production procedure of the new compound was found. The new compound can be used as an effective component of anti-amnestic agent and is useful for the preparation of preventive and treatment agents against acquired immunodeficiency syndrome (AIDS) and anti-HIV agents. Furthermore, it was discovered that cleavage of the only one carboxyl site of arginine in the inhibitor by a pro tease such as trypsin and arginylendopeptidase provides a new straight chain prolyl endopeptidase inhibitor having different chemical properties and biological activities with those of the aforementioned inhibitor.

Thus, one object of the present invention is to provide new peptides having prolyl endopeptidase inhibitory activity.

Other object of the present invention is to provide microorganisms that can produce such prolyl endopeptidase inhibitor.

One other object of the present invention is to provide a process for the production of the peptides having prolyl endopeptidase inhibitory activity using such microorganisms.

The inventors searched prolyl endopeptidase inhibitor productive microorganisms from soil samples throughout Japan and found a highly endopeptidase inhibitor productive microorganism in a soil sample obtained from about 1 cm depth at Miura peninsula, Kanagawa Prefecture and isolated the microorganism.

In more detail, the inventors collected a sample from about 1 cm depth of soil at Miura peninsula, Kanagawa Prefecture and the soil sample was stored in the air under saturated humidity, then heated at 60° C. The treated soil sample was diluted with sterilized water, sonicated to extract microorganisms. The extracted solution was spread onto an isolation medium and cultured to screen and isolate the aforementioned microorganism. The microorganism was cultured to give a product and the product was subjected to an enzyme reaction using Z-Gly-Pro-pNA (Z and pNA mean benzyloxycarbonyl group and p-nitroaniline, respectively) as a substrate in the presence of prolyl endopeptidase. The concentration of released p-nitroaniline was comparatively determined with that of a control group to determine the prolyl endopeptidase inhibitory activity [Agric. Biol. Chem., 54, 3021–3022 (1990)]. The product of the isolated micro-organism exhibited a markedly stronger prolyl endopeptidase inhibitory activity than those of microorganisms isolated from soil samples collected in the other places.

The mycological properties were investigated and the following properties were found:

1) Morphological Properties

Observation with scanning electron microscope showed characteristic two spores adjacent on the aerial mycelia. The spores were short cylindrical having diameter of 1.1–1.3μ and length of 1.3–1.7μ with smooth surface.

2) Growth on Various Media

Culture of the microorganism at 27° C. for 3 weeks in 9 agar media of sucrose.nitrate, glucose.asparagine, ISP No. 5 (glycerol.asparagine), ISP two. 4 (inorganic salts.starch), ISP No. 7 (tyrosine), nutrient, ISP No. 2 (yeast extract.malt extract), ISP No. 3 (oatmeal) and ISP No. 6 (peptone.yeast extract.iron) resulted in the best growth in a yeast extract.malt extract agar medium and ISP No. 3 (oatmeal) as shown in Table 1. However, poor growth of aerial and substrate mycelia was observed in all media. The adherence of spores was satisfactory in glycerol.asparagine and tyrosine agar media, and substrate mycelia showed yellowish brown in yeast extract.malt extract and oatmeal agar media.

TABLE 1

Growth of mycelia in various media

| Medium | Day of culture | | | |
|---|---|---|---|---|
| | 3 | 7 | 14 | 21 |
| Sucrose nitrate | − | ± | + | + |
| Glucose . asparagine | − | ± | + | + |
| Glycerol . asparagine | − | + | + | + |
| Inorganic salts . starch | − | ± | + | + |
| Tyrosine | − | + | + | + |
| Nutrients | − | ± | + | + |
| Yeast extract . malt extract | − | + | + | ++ |
| Oatmeal | − | ± | + | ++ |
| Peptone . yeast extract . iron | − | ± | + | + |

−0 No growth, ±) Very poor growth, +) Poor growth, ++) Slight growth

3) Physiologic properties a) Growth temperature; The growth was observed at temperature of 22–47° C. in yeast malt agar medium, and the optimal temperature was about 40° C. (Table 2).
b) Liquefaction of gelatin; Negative
c) Hydrolysis of starch; Negative
d) Peptonizatione . coagulation of skimmed milk; Negative
e) Formation melanin-like pigment; Negative

TABLE 2

Influence of temperature on the growth

| Temperature (°C.) | Days | | | |
|---|---|---|---|---|
| | 3 | 7 | 14 | 21 |
| 17 | − | − | − | − |
| 22 | − | − | ± | + |
| 27 | − | + | + | ++ |
| 32 | + | + | ++ | |
| 37 | + | ++ | | |
| 42 | ++ | | | |
| 47 | ++ | | | |
| 52 | − | − | − | − |

−) No growth, ±) Very poor growth, +) Poor growth, ++) Slight growth

4) Assimilation of Carbon Sources

Assimilation was observed in PPIDHAM-GOTTLIEB® medium added with 1% each of one of 11 compounds of L-arabinose, D-xylose, D-glucose, D-fructose, sucrose, inositol, L-rhamnose, raffinose, D-mannitol, salicin and D-galactose. The assimilation was slight in all media (Table 3).

TABLE 3

Assimilation of various carbon source

| Carbon source | Days | | | |
|---|---|---|---|---|
| | 3 | 7 | 14 | 21 |
| L-Arabinose | − | ± | ± | ± |
| D-Xylose | − | ± | ± | ± |
| D-Glucose | − | ± | ± | ± |
| D-Fructose | − | ± | ± | ± |
| Sucrose | − | ± | ± | ± |
| Inositol | − | ± | ± | ± |
| L-Rhamnose | − | ± | ± | ± |
| Raffinose | − | ± | ± | ± |
| D-Mannitol | − | ± | ± | ± |
| Salicin | − | ± | ± | ± |
| D-Galactose | − | ± | ± | ± |

−) No growth, ±) Very poor growth, +) Poor growth, ++) Slight growth

5) Composition of Cell Wall

Analysis of 2,6-diaminopimelic acid in the cells of SNA-115 strain by the method of Lechevalier et al. [int. J. Syst. Bacteriol., 20, 435–443 (1970)] revealed its meso type structure (cell wall type III).

Above microscopic observations and analysis of cell wall composition suggested the SNA-115 strain to be one of Microbispora sp. and named Microbispora sp. SNA-115. Its physiological investigation according to the Bergey's Manual of Systematic Bacteriology Vol. 4 suggested the similarity with those of *Microbispora rosea*.

The inventors deposited the SNA-115 strain with the Agency of Industrial Science and Technology, Fermentation Research Institute as FERM P-12094.

As described above, the SNA-115 strain resembled *Microbispora rosea*, thus the inventors compared the inhibitory activities of SNA-115 with those of some available official Microbispora strains, Similar activities were found in *Microbispora rosea* Nonomura and Ohara (IFO 14044), *Microbispora rosea* subsp. nonnitritogenes Nonomura and Ohara (IFO 14045) and *Microbispora indica* (IFO 14879). The active fractions of these three strains were analyzed with high performance liquid chromatography (HPLC) and their retention times were identical with that of SNA-115, thus their products were identical with SNA-115. Therefore, the SNA-115 productive Microbispora sp. official strains shall be within the scope of the present invention.

The SNA-115 strain grows in almost similar manners with those of known strains but showed different chromogenic property in the growth in the medium ISP No. 7.

The Microbispora sp. SNA-115 strain was inoculated in a liquid medium composed of 2% glucose, 1% soluble starch, 2.5% soybean flour, 0.1% meat extract, 0.4% dried yeast, 0.2% NaGl and 0.005% $K_2HPO_4$, pasteurized in an autoclave and adjusted to pH 7.0. The inoculated medium was pre- and main-cultured aerobically with shaking or stirring at 27° C. to proliferate the cells and the prolyl endopeptidase inhibitor was isolated from the collected cells. The active component in the collected cells was extracted with an organic solvent, the extract was suspended in a mixture of chloroform and methanol (2:1) and subjected to a silica gel column chromatography. The adsorbed product was eluted with mixtures of chloroform and methanol at ratios of 1:1 and then 1:2. The combined eluate was subjected to a column chromatography using SEPHADEX® LH-20 (Pharmacia AB, Sweden) and developed with an organic solvent, preferably acetone or methanol to give an active fraction. The active fraction was subjected to HPLC and the eluted active fraction was condensed and lyophilized to give white powder.

The physicochemical properties of the white powder were analyzed. The fraction was identified as a new peptide and named SNA-115.

Physicochemical Properties:

| 1) Elemental analysis | | | |
|---|---|---|---|
| | C | H | N |
| Analyzed (%) | 54.35 | 5.72 | 13.41 |

2) Molecular formula $C_{113}H_{142}N_{26}O_{27}$

3) High resolution mass spectrum (HRFAB-MS)
Analyzed $(M+H)^+ = 2296.0549$ Calculated $(M+H)^+ = 2296.0616$ 4) Melting point No definite melting point was observed but the compound changed brown at 230°–240° C. and decomposed.

5) Specific rotation $[\alpha]_D^{24} = -87°$ (c=0.1, methanol)

6) UV absorption spectrum Shown in FIG. 1. $\lambda_{max}^{MeOH}$ ($\epsilon$)=280 (11934)

7) IR absorption spectrum (KBr method) Shown in FIG. 2.

8) $^1$H NMR spectrum (400 MHz) Shown in FIG. 3. TMS in deuterated dimethylsulfoxide was used as a standard substance.

9) $^{13}$C NMR spectrum (100 MHz) Shown in FIG. 4. TMS in deuterated dimethylsulfoxide was used as a standard substance.

10) Solubility Soluble in methanol, dimethylsulfoxide, butanol and ethanol, and insoluble in acetonitrile, chloroform, acetone and water.

11) Appearance White powder

12) Thin layer chromatography Carrier: Silica gel plate F254 Art. 5715 (E. Merck)

| Developing solvent | Rf value |
|---|---|
| Butanol/methanol/water (4:1:2) | 0.36 |

13) Amino acid analysis SNA-115 is a peptide and amino acid analysis of SNA-115 with an amino acid autoanalyzer after hydrolysis with 4N methanesulfonic acid at 90° C. for 24 hrs. detected asparttic acid (or asparagine) (2), threonine (1), serine (1), glycine (3), isoleucine (1), leucine (1), tyrosine (2), phenylalanine (2), histidine (1), arginine (1), proline (2) and tryptophan (2), (numerals in parentheses indicate molar ratio).

Structure determination based on Edman degradation, analysis of fragment ion of FAB-MS spectrum, and linked scan of FAB-MS gave the peptide structure shown by the structural formula (I). The peptide was named SNA-115 (propeptin).

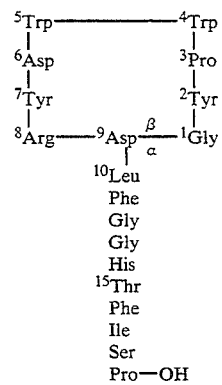

The prolyl endopeptidase inhibitory activity, cytotoxicity (human epidermoid carcinoma (oral) cell EB, mouse leukemia cell L1210), and antimicrobial activity of the prolyl endopeptidase inhibitor SNA-115 of the present invention were determined as follows:

1) Prolyl endopeptidase inhibitory activity

The determination of the enzyme inhibitory activity is shown below. In 0.84 ml of 0.1M Tris HCl buffer (pH 7.0), 0.01 ml of various concentrations of the sample in methanol and 0.05 ml of prolyl endopeptidase (0.1 unit/ml) derived from Flavobacterium (Seikagaku Kogyo Co.) dissolved in 0.1M Tris HCl buffer (pH 7.0) were added and the mixture was kept at 30° C. for 5 min. The resultant mixture was added with 0.1 ml of a synthetic substrate Z-Gly-Pro-pNA (Seikagaku Kogyo Co.) dissolved in 40% dioxane (2 mM solution) and caused to react at 30° C. for 30 min. After the reaction was terminated with addition of 0.5 ml of a termination solution (10 g of Triton X-100 in 95 ml of 1M acetate buffer, pH 4.0) the liberated p-nitroaniline was colorimetrically determined at 410 nm. The inhibitory rate was shown by the following equation:

$$\frac{(A - B)}{A} \times 100(\%)$$

In the equation,
A: Absorption of liberated p-nitroaniline at 410 nm by the control reaction added with the equal amount of methanol in the absence of the sample.
B: Absorption of liberated p-nitroaniline at 410 nm in the presence of the sample.

The 50% inhibitory concentration (IC$_{50}$) of SNA-115 methanol solution determined by the reaction condition shown above using 0.2 mM Z-Gly-Pro-pNA as the substrate was 2.6 $\mu$g/ml (1.1 $\mu$M). The inhibitory activities were analyzed under various concentrations of the substrate and SNA-115, and the inhibitory pattern was investigated with the Dixon Plot. SNA-115 showed competitive inhibition and its inhibitor constant obtained from the Fig. was Ki=1.6 $\mu$g/ml (0.7 $\mu$M) (FIG. 5).

2) Cytotoxicity

Human epidermoid carcinoma (oral) KB cells and mouse leukemia L1210 cells each were placed in a 96 wells microplate (2,000 cells/100 $\mu$l/well). The former cells were cultured in DMEM medium and the latter cells were cultured in RPMI 1640 medium, each containing 5% FCS. They were cultured in the presence of 5% CO$_2$ at 37° C. for 24 hrs. Five $\mu$l each of a serial concentration of SNA-115 in methanol were added to the wells and cultured for 72 hrs. and cultured further 4 hrs. after the addition of 10 µl of 2.5 mg/ml MTT solution to produce formazan. The cultured mixture was centrifuged at 2,000 rpm for 2 min., the supernatant was removed, 100 µl of DMSO was added to the residue and the absorption at 540 nm was determined by an immunoreader. The cell proliferation inhibitory activity of samples was obtained from comparison of their ratios to that of control group. The results are shown in Table 4.

TABLE 4

| Inhibitory effect of SNA-115 against cell proliferation | |
|---|---|
| Test cells | $IC_{50}$ (µg/ml) |
| Human epidermoid carcinoma (oral) KB | >1,000 |
| Mouse leukemia L1210 | >1,000 |

3) Antimicrobial activity

The antimicrobial activity of SNA-115 was determined in 24 bacteria, fungi, and yeasts by paper disc method. SNA-115 was placed on paper discs at an amount of 40 µg each and the disc was placed on the test plates. The test plates were cultured under optimal conditions of the test microorganisms. The produced diameters of inhibition zone (mm) are shown in the Table 5.

TABLE 5

| The inhibitory effect of SNA-115 to various microorganisms | |
|---|---|
| Microorganism | Inhibition zone (mm) |
| Bacteria | |
| Escherichia coli AB 1157 | 0 |
| Escherichia coli BE 1186 | 0 |
| Escherichia coli multi resistant | 0 |
| Salmonella typhimurium TV 119 | 0 |
| Salmonella typhimurium SL 1102 | 0 |
| Pseudomonas aeruginosa IFO 13130 | 0 |
| Pseudomonas aeruginosa N-10 (L-form) | 10.6(15.2) |
| Staphylococcus aureus IFO 12732 | 0 |
| Staphylococcus aureus multi resistant | 0 |
| Bacillus subtilis rec+ | 0 |
| Bacillus subtilis rec− | (15.2) |
| Micrococcus luteus IFO 12708 | 0 |
| Mycobacterium phlei IFO 3158 | 14.5 |
| Xanthomonas oryzae IFO 3312 | 11.5 |
| Xanthomonas citri IFO 3781 | 0 |
| Fungi | |
| Alternaria mali IFO 8984 | 0 |
| Botrytis cinerea IFO 5365 | 0 |
| Colletotrichum lagenarium IFO 7513 | 0 |
| Pyricularia oryzae IFO 5994 | 0 |
| Fusarium oxysporum IFO 9761 | 0 |
| Trichophyton rubrum IFO 6203 | 0 |
| Yeasts | |
| Candida albicans IFO 1594 | 0 |
| Schizosaccharomyces Pombe IFO 0638 | 0 |
| Chlorella vulgaris | 0 |

( ) indicates partial inhibition

As shown above, the prolyl endopeptidase inhibitor SNA-115 of the present invention has very weak cytotoxicity and antimicrobial activity and has specifically potent prolyl endopeptidase inhibitory activity. Thus the compound will be very useful as anti-amnestic agent and antiviral agent including agents for the prevention and treatment of acquired immunodeficiency syndrome (AIDS) and anti-HIV agent.

Furthermore, the carboxyl site of arginine in SNA-115 of the present invention was cleaved with a protease such as trypsin or argininylendopeptidase to make a straight peptide chain and a new prolyl endopeptidase inhibitor having different chemical and biological properties from those of SNA-115 was found and was named SNA-115T. SNA-115T has the following structural formula (II) and specifically enhanced inhibitory activity to prolyl endopeptidase without any antimicrobial activity.

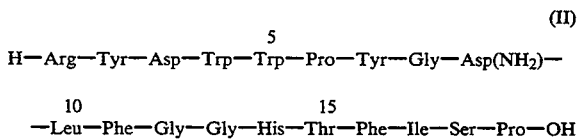

(II)

Physicochemical properties of SNA-115T are shown below:

1) Molecular formula $C_{113}H_{144}N_{26}O_{28}$
2) Mass spectrum (FAB-MS) Analyzed $(M+H)^+ = 2314$ Shown in FIG. 6.
3) High resolution mass spectrum (HRFAB-MS) Analyzed $(M+H)^+ = 2314.0740$ Calculated $(M+H)^+ = 2314.0722$
4) Melting point No definite melting point was observed but the compound changed brown at 190°–200° C. and decomposed.
5) Specific rotation $[\alpha]_D^{24} = -47°$ (c=0.2, methanol)
6) UV absorption spectrum $\lambda_{max}^{MeOH}$ nm ($\epsilon$)=280 (11149) Shown in FIG. 7.
7) IR absorption spectrum (KBr method) Shown in FIG. 8.
8) $^1$H NMR spectrum (500 MHz) Shown in FIG. 9. TMS in deuterated dimethylsulfoxide was used as a standard substance.
9) Solubility Soluble in methanol, dimethylsulfoxide, butanol and ethanol, and insoluble in chloroform, acetone and water.
10) Appearance White powder
11) Thin layer chromatography Carrier: Silica gel plate F254 Art.5715 (E. Merck)

| Developing solvent | Rf value |
|---|---|
| Butanol/methanol/water (4:1:2) | 0.30 |

12) Amino acid analysis SNA-115T is a peptide and amino acid analysis of SNA-115T with an amino acid autoanalyzer after hydrolysis with 4N methanesulfonic acid at 90° C. for 24 hrs. showed aspatic acid (or asparagine) (2), threonine (1), serine (1), glycine (3), isoleucine (1), leucine (1), tyrosine (2), phenylalanine (2), histidine (1), arginine (1), proline (2) and tryptophan (2). Structure determination based on Edman degradation, analysis of fragment ion of FAB-MS spectrum, and linked scan of FAB-MS gave the peptide structure shown by structural formula (II).

The prolyl endopeptidase inhibitory activity and antimicrobial activity of the prolyl endopeptidase inhibitor SNA-115T of the present invention were determined as follows:

1) Prolyl endopeptidase inhibitory activity

The determination of the enzyme inhibitory activity is shown below. In 0.84 ml of 0.1M Tris HCl buffer (pH 7.0), 0.01 ml of various concentrations of the sample in methanol and 0.05 ml of prolyl endopeptidase (0.1 unit/ml) derived from Flavobacterium (Seikagaku Kogyo Co.) dissolved in 0.1M Tris HCl buffer (pH 7.0) were added and the mixture was kept at 30° C. for 5 min. The resultant mixture was added with 0.1 ml of the synthetic substrate Z-Gly-Pro-pNA (Seikagaku Kogyo Co.) dissolved in 40% dioxane (2 mM solution) and caused to react at 30° C. for 30 min. After the reaction was terminated with addition of 0.5 ml of a terminating solution (10 g of TRITON® X-100 in 95 ml of 1M acetate buffer, pH 4.0), the liberated p-nitroaniline was colorimetrically determined at 410 nm. The inhibitory rate was shown by the following equation:

$$\frac{(A - B)}{A} \times 100(\%)$$

In the equation,
A: Absorption of liberated p-nitroaniline at 410 nm by the control reaction added with the equal amount of methanol in the absence of the sample.
B: Absorption of liberated p-nitroaniline at 410 nm in the presence of the sample.

The 50% inhibitory concentration ($IC_{50}$) of SNA-115T methanol solution determined by the reaction condition shown above using 0.2 mM Z-Gly-Pro-pNA as the substrate was 3.0 μg/ml (1.3 μM), The inhibitory activities were analyzed under various concentrations of the substrate and SNA-115T and the inhibitory pattern was investigated with the Dixon Plot. SNA-115T showed competitive inhibition and its inhibitor constant obtained from the Fig. was Ki=1.1 μg/ml (0.48 μM) (FIG. 10).

2) Antimicrobial activity

The antimicrobial activity of SNA-115T compound was determined in 9 bacteria and fungi by paper disc method in an agar plate. SNA-115T was placed on paper discs at an amount of 40 μg each and the disc was placed on the test plates. The test plates were cultured under optimal conditions of the rest microorganisms. The produced diameters of inhibition zone (mm) are shown in the Table 6. The inhibition zones of SNA-115 were also shown for the comparison.

TABLE 6

The inhibitory effect of SNA-115T to various microorganisms

| Microorganism | Inhibition zone (mm) | |
| --- | --- | --- |
|  | SNA-115T | SNA-115 |
| Salmonella typhimurium SL 1102 | 0 | 0 |
| Pseudomonas aeruginosa N-10 (L-form) | 0 | 16.8 |
| Bacillus subtilis rec+ | 0 | 0 |
| Bacillus subtilis rec− | 0 | 0 |
| Mycobacterium phlei IFO 3158 | 0 | 13.8 |
| Xanthomonas oryzae IFO 3312 | 0 | + |
| Xanthomonas citri IFO 3781 | 0 | 0 |
| Botrytis cinerea IFO 5365 | 0 | 0 |
| Pyricularia oryzae IFO 5994 | 0 | 0 |

(+ indicates inhibitory zone diameter of 10 mm or less)

As shown above, the prolyl endopeptidase inhibitor SNA-115T of the present invention markedly decreased the antimicrobial activity compared to that of SNA-115 and has specifically potent prolyl endopeptidase inhibitory activity. Thus the compound will be very useful as anti-amnestic agent and antiviral agent including agents for the prevention and treatment of acquired immunodeficiency syndrome (AIDS) and anti-HIV agent.

The peptide is a new compound.

The prolyl endopeptidase inhibitors SNA-115 and SNA-115T can be prepared as tablets, powder preparations, capsules, injections, inhalants and external preparations by conventional methods. The resultant pharmaceutical preparations can be provided for Clinical use as anti-amnestic or anti-viral agents by oral or parenteral route. The dosage may be changed with the symptoms and responses of the patients and route of administration. The acute toxicities of both prolyl endopeptidase inhibitors SNA-115 and SNA-115T was 10 mg/kg or over (intravenous injection), respectively.

THE BEST MODE OF THE PRESENT INVENTION

Figure 1:
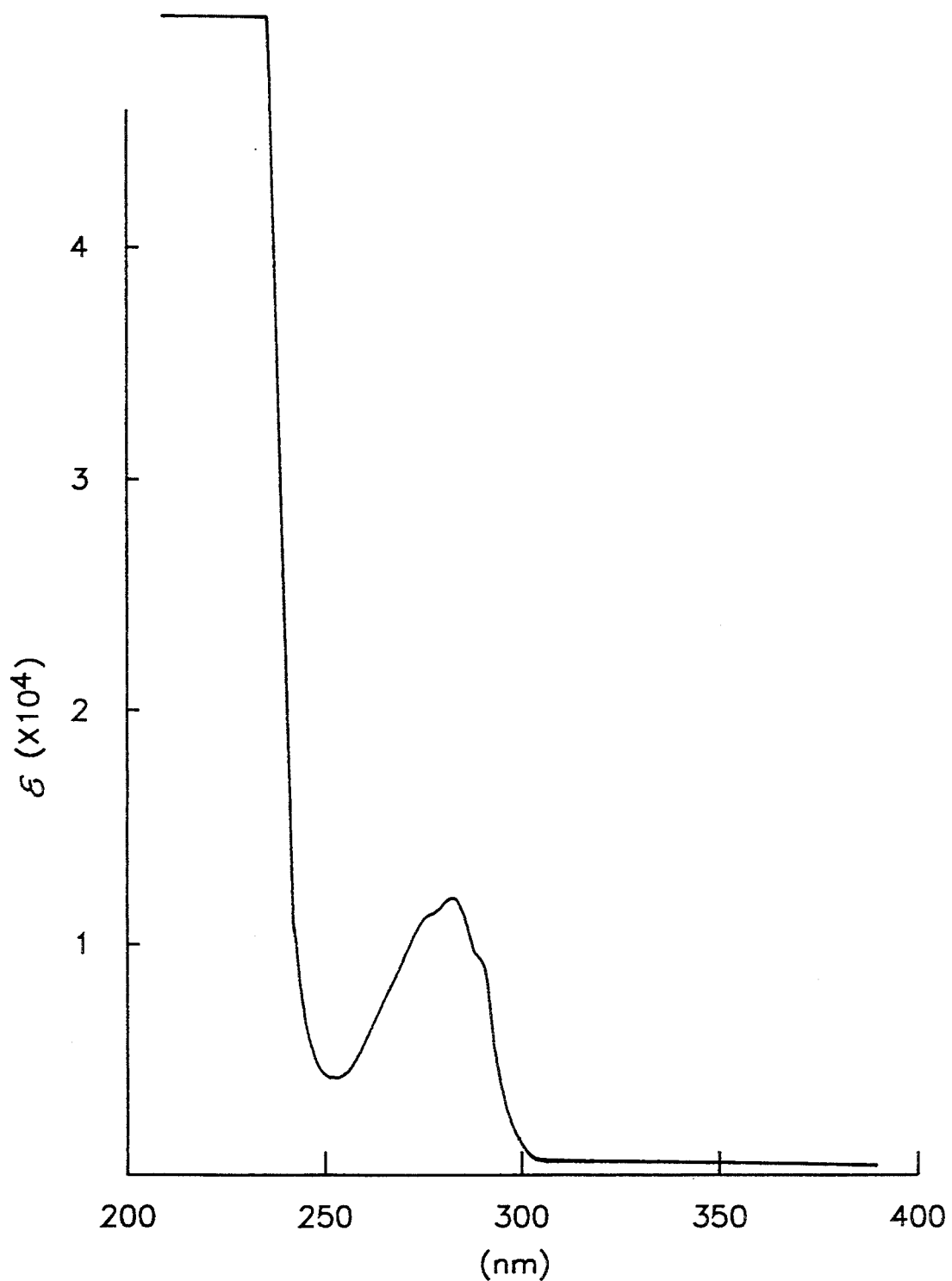
FIG. 1 shows UV absorption spectrum of prolyl endopeptidase inhibitor SNA-115 (50 μg/ml, MeOH).
Figure 2:
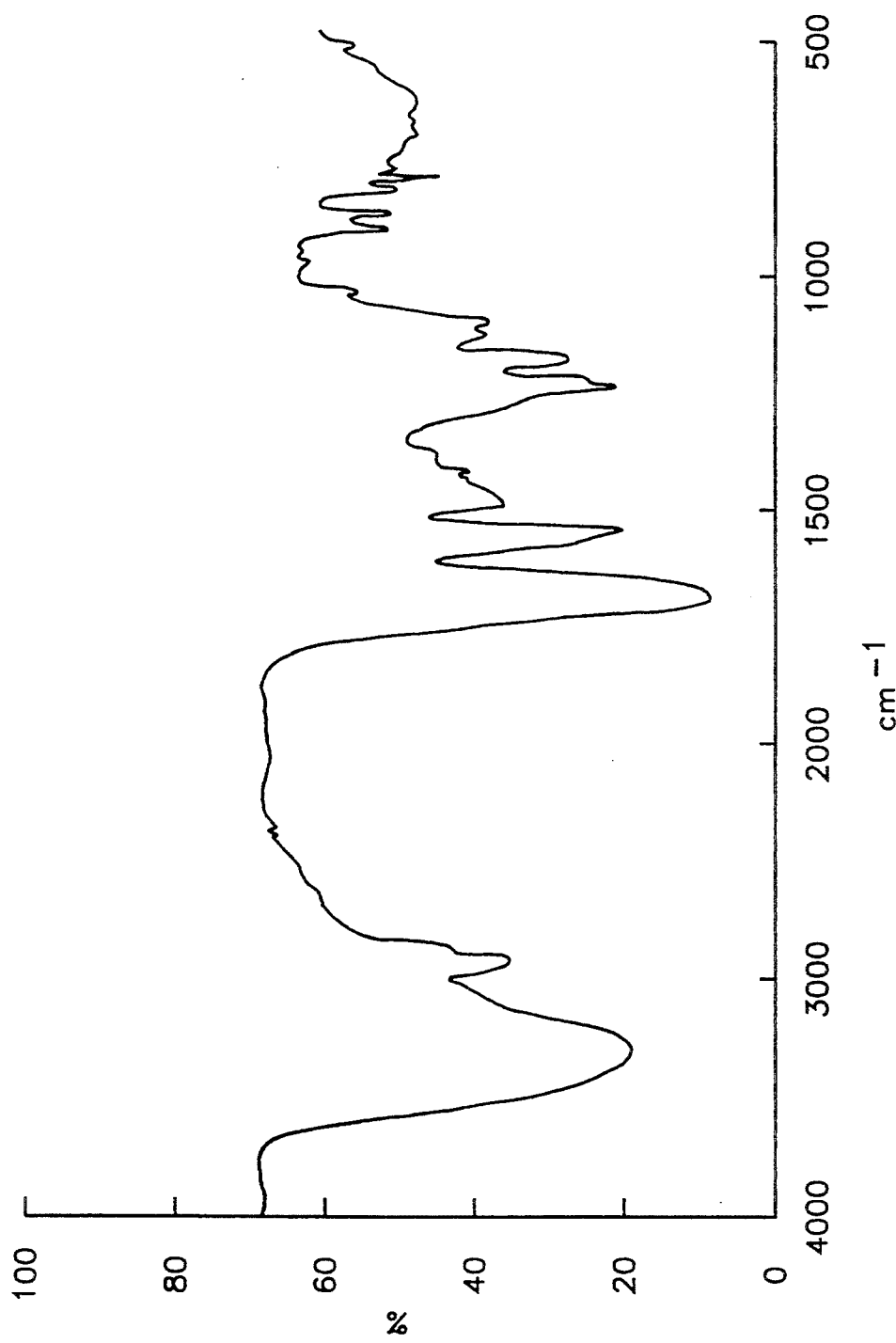
FIG. 2 shows IR absorption spectrum of prolyl endopeptidase inhibitor SNA-115 (KBr).
Figure 3:
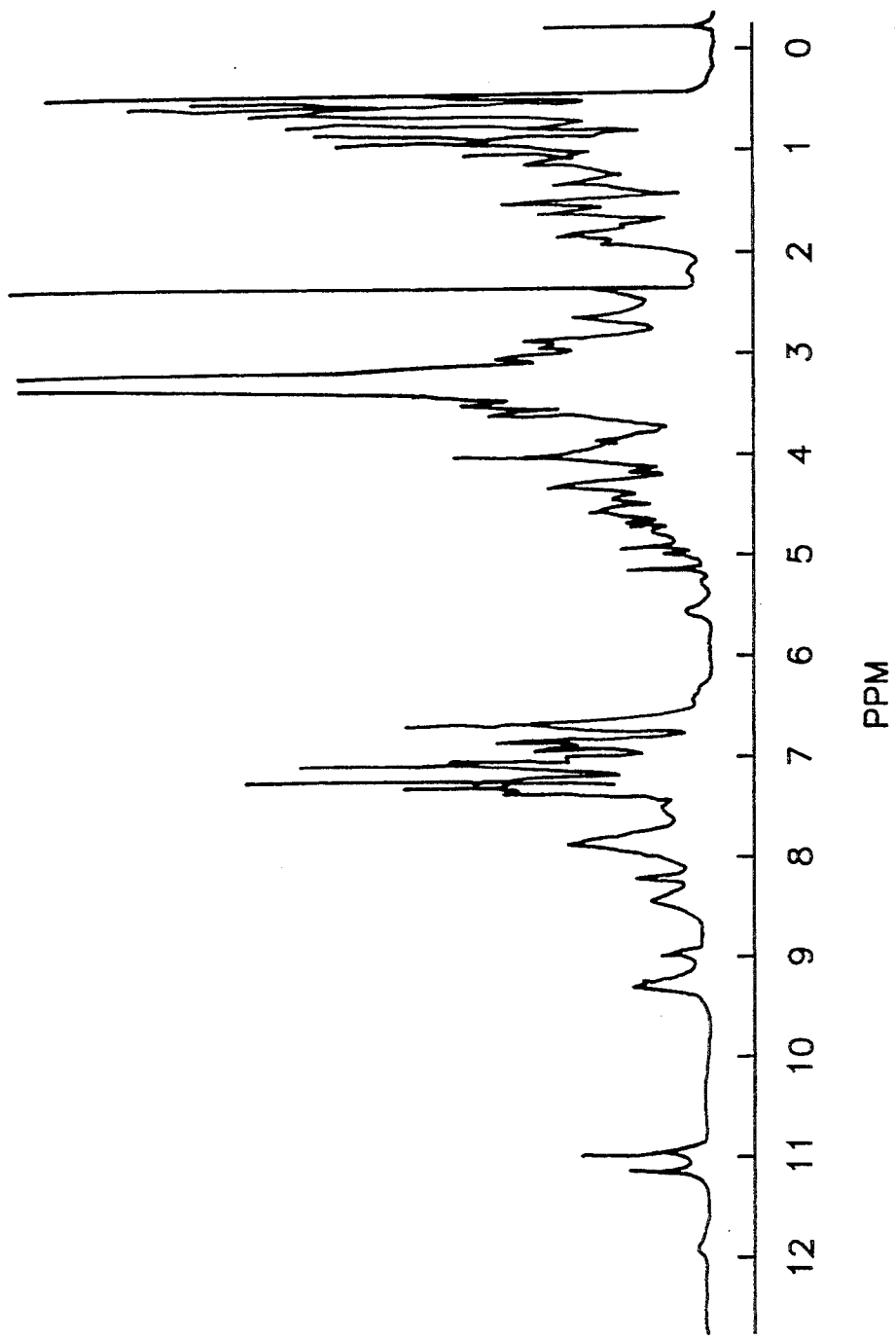
FIG. 3 shows $^1H$ NMR spectrum of prolyl endopeptidase inhibitor SNA-115 (400 MHz, $C_2D_6OS$).
Figure 4:
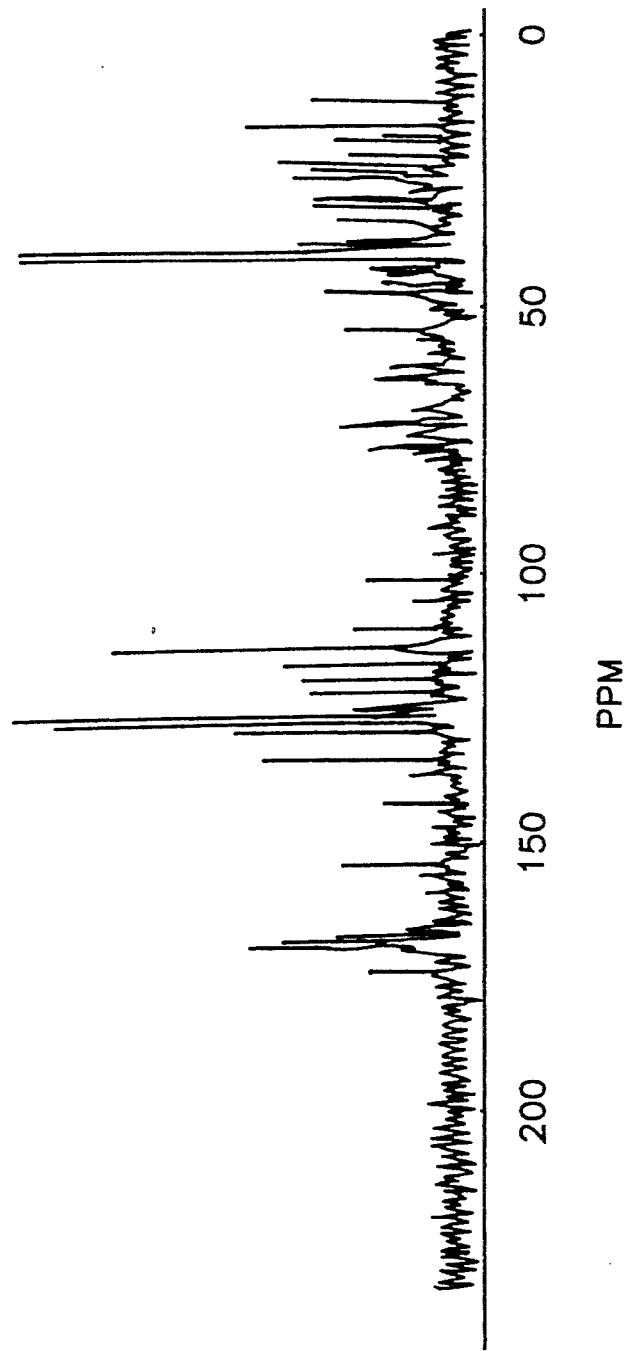
FIG. 4 shows $^{13}C$ NMR spectrum of prolyl endopeptidase inhibitor SNA-115 (100 MHz, $C_2D_6OS$).
Figure 5:
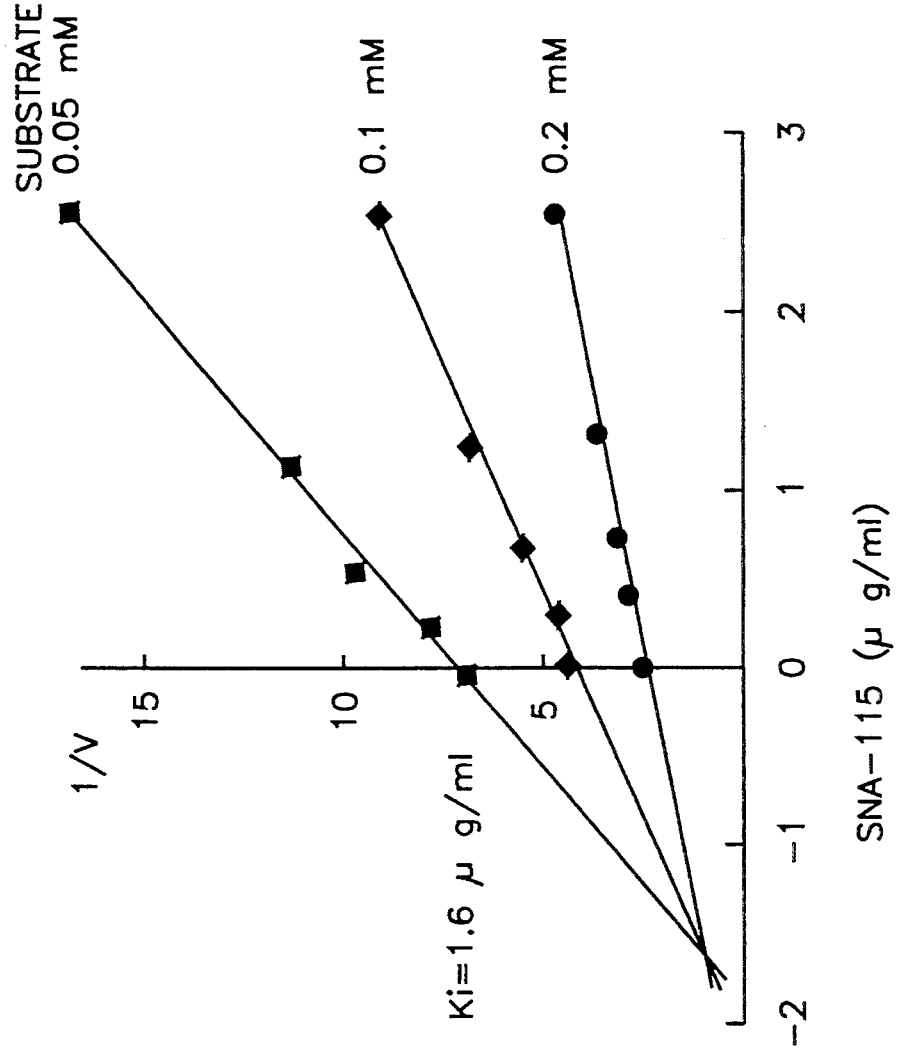
FIG. 5 shows Dixon plot of prolyl endopeptidase inhibitory activity of prolyl endopeptidase inhibitor SNA-115 (1/V means 1/Δ 410 nm).
Figure 6:
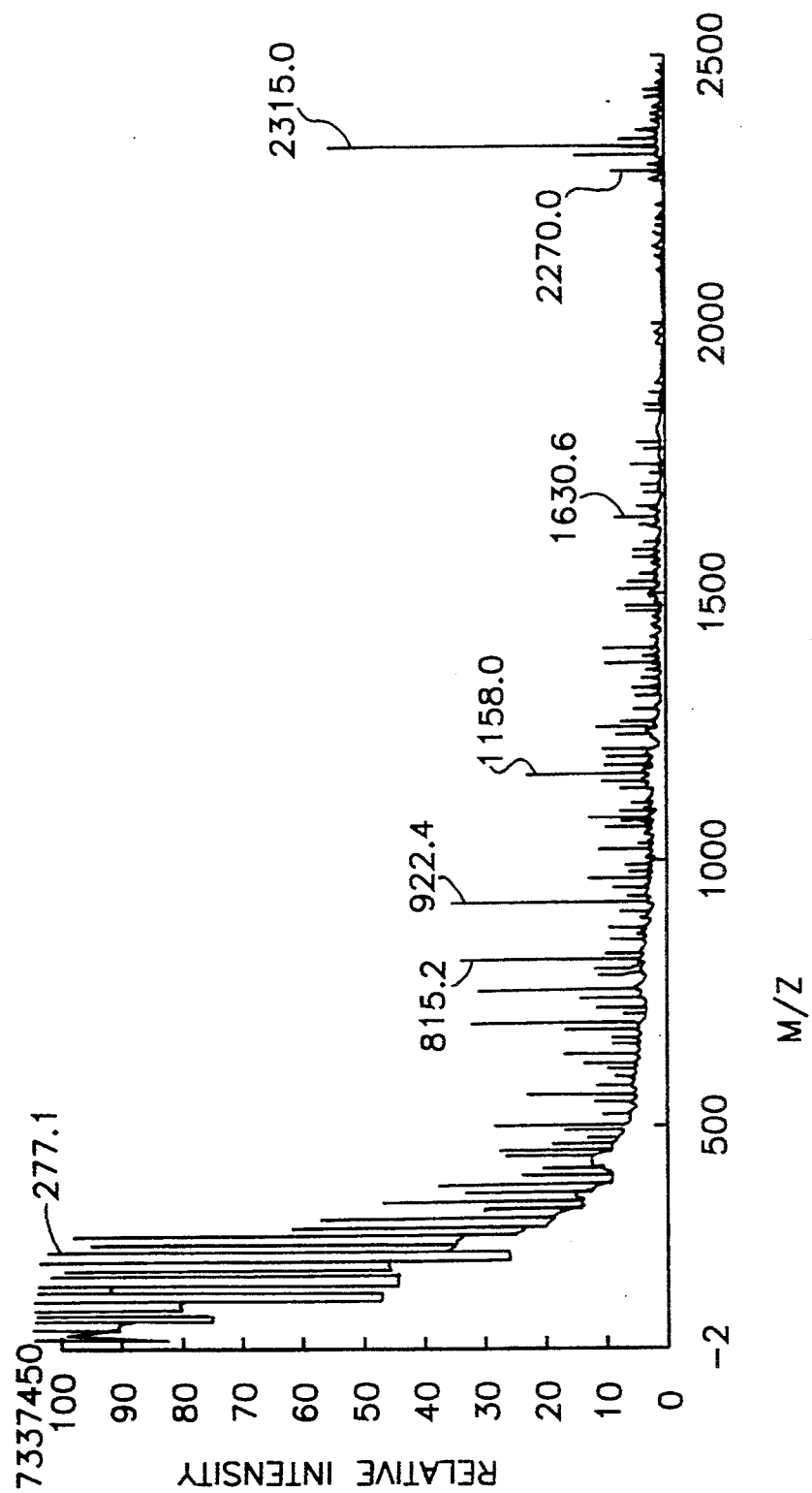
FIG. 6 shows mass spectrum of prolyl endopeptidase inhibitor SNA-115T (FAB-MS).
Figure 7:
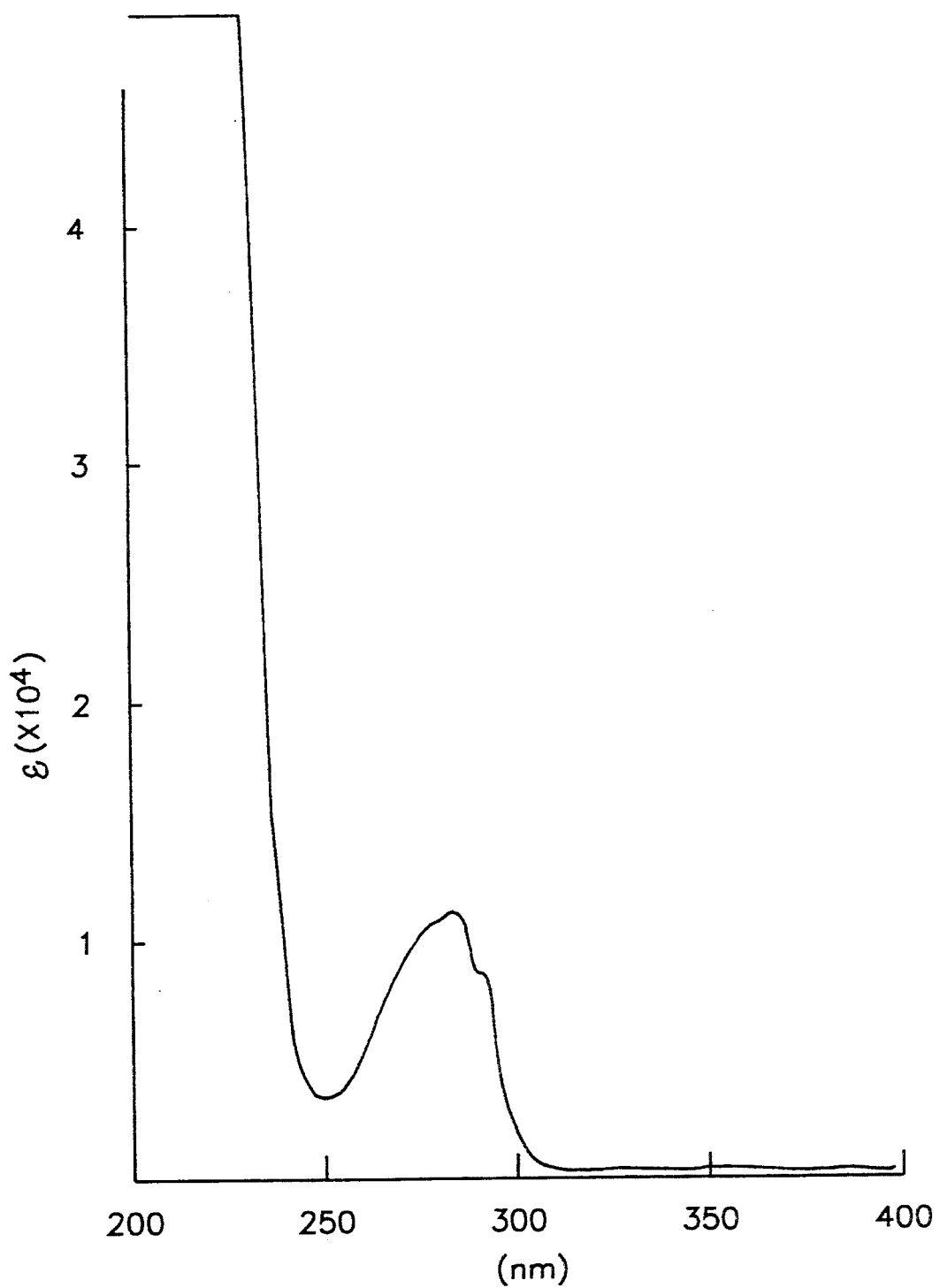
FIG. 7 shows UV absorption spectrum of prolyl endopeptidase inhibitor SNA-115T (50 μg/ml, MeOH).
Figure 8:
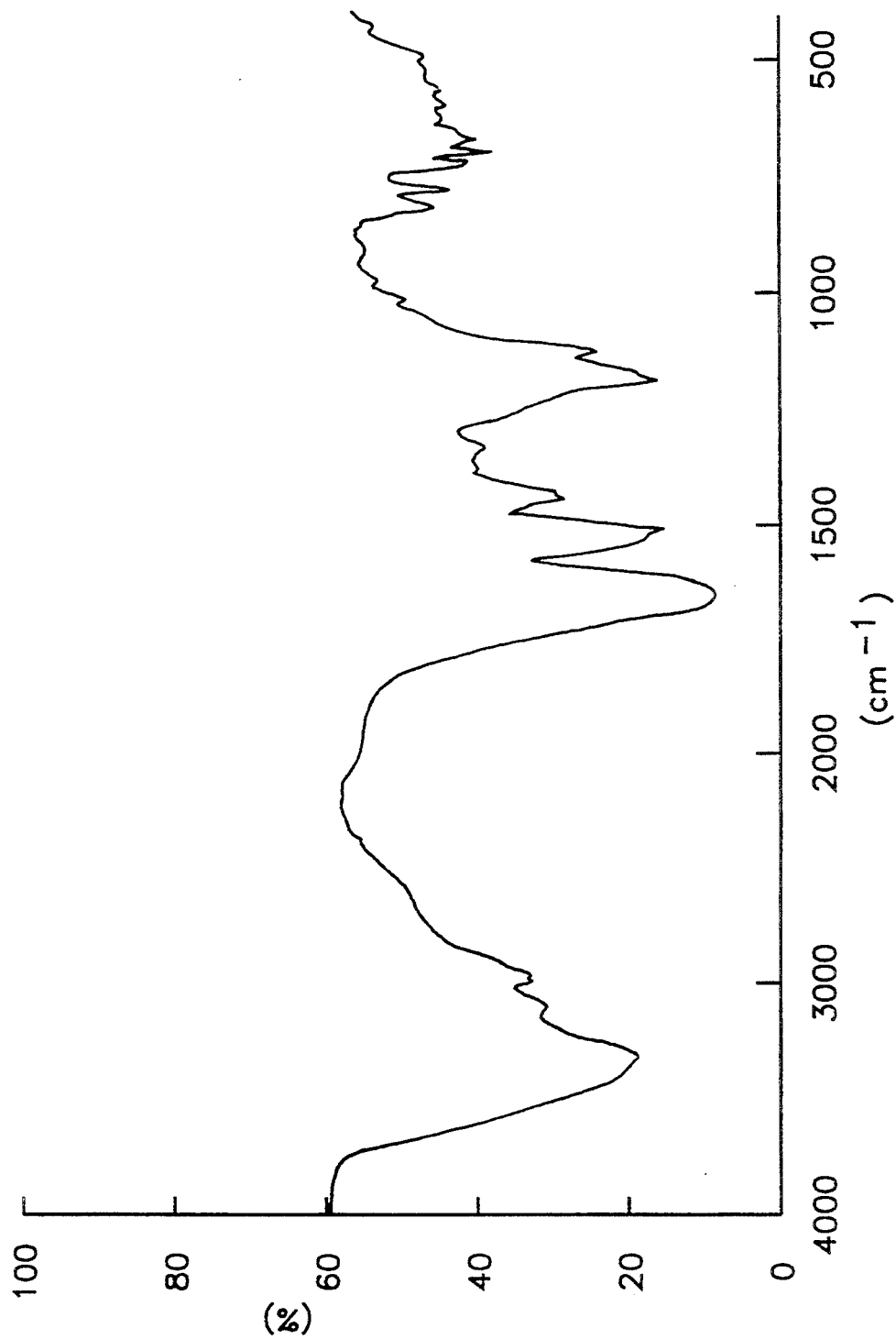
FIG. 8 shows IR absorption spectrum of prolyl endopeptidase inhibitor SNA-115T (KBr).
Figure 9:
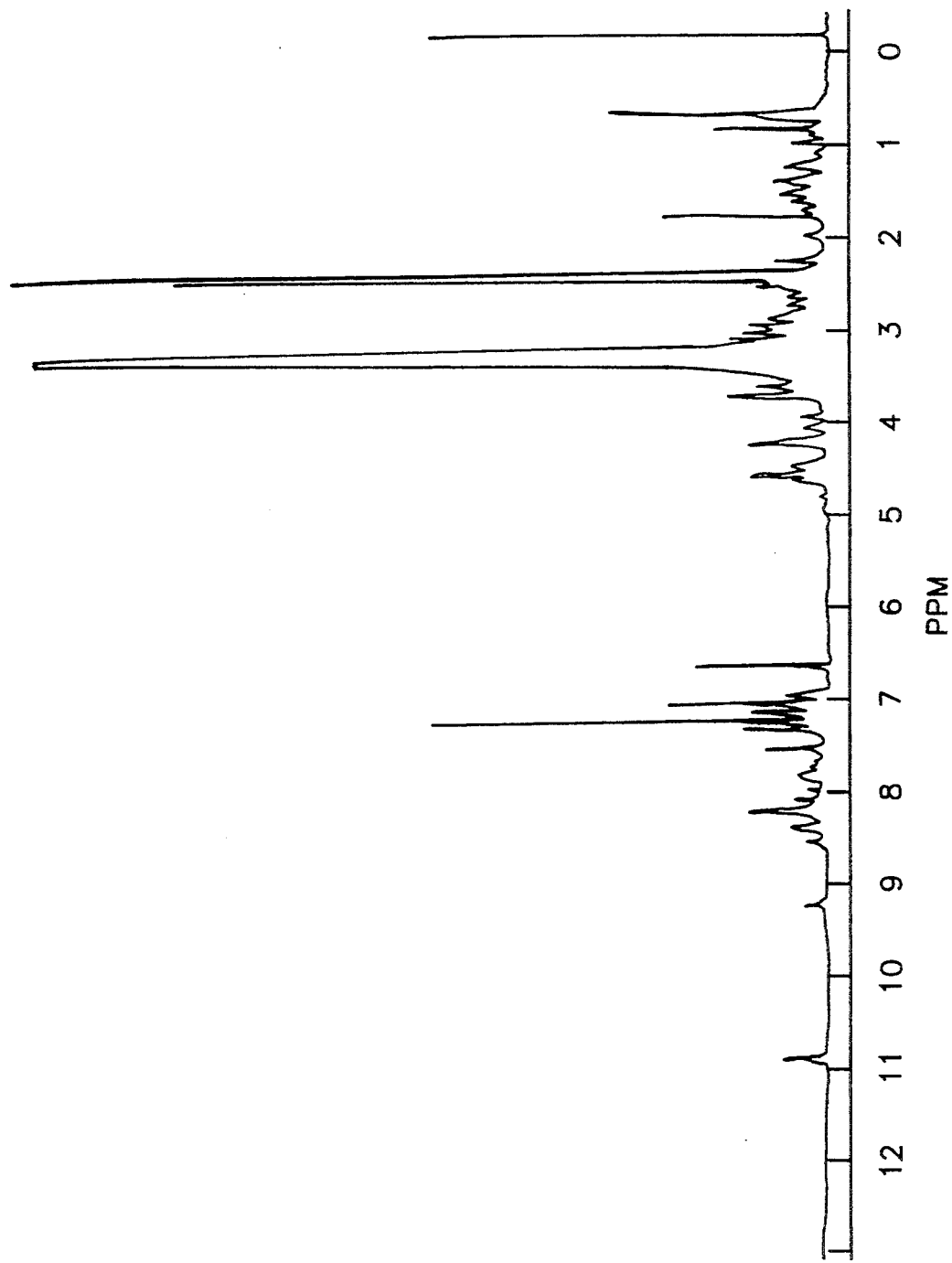
FIG. 9 shows $^1H$ NMR spectrum of prolyl endopeptidase inhibitor SNA-115T (500 MHz, $C_2D_6OS$).
Figure 10:
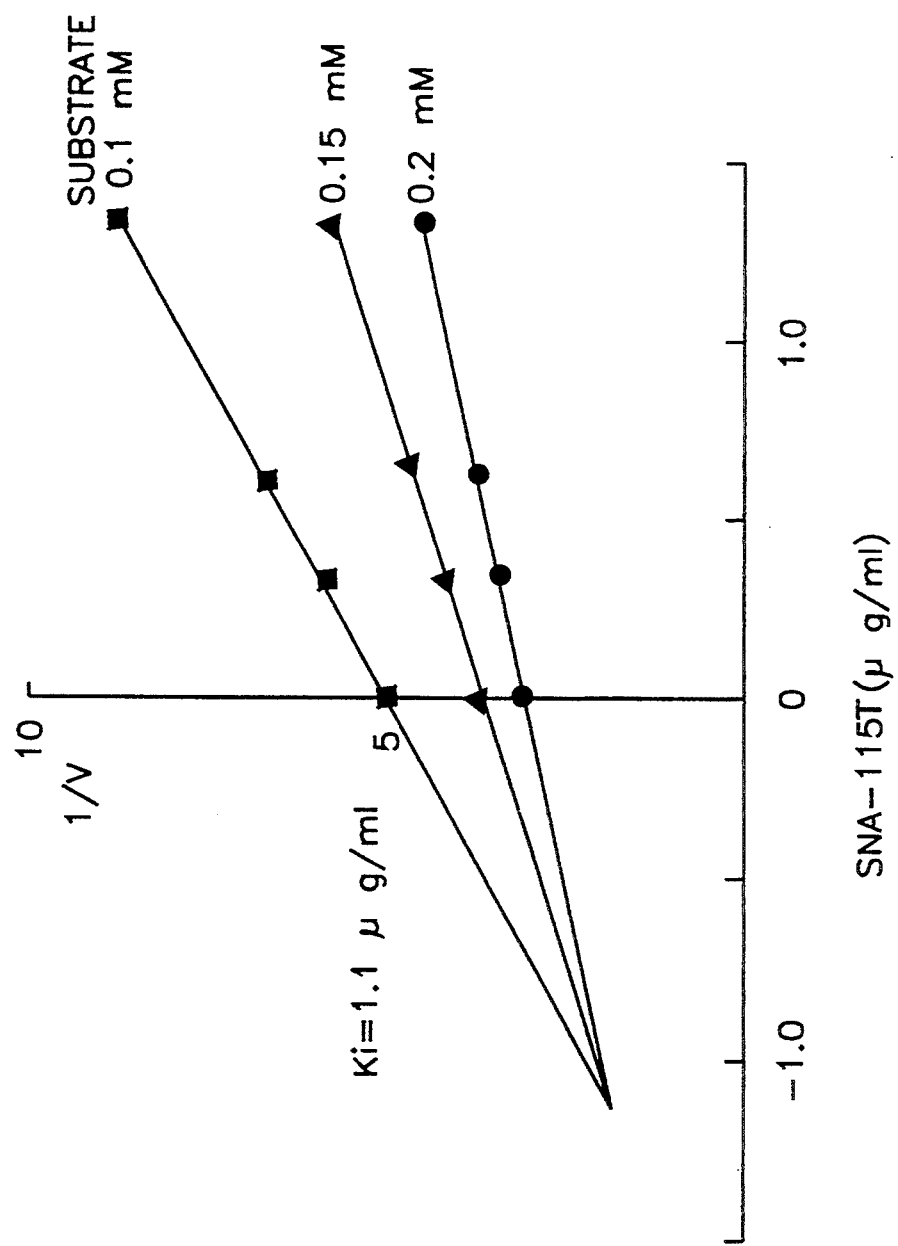
FIG. 10 shows Dixon plot of prolyl endopeptidase inhibitory activity of prolyl endopeptidase inhibitor SNA-115T (1/V means 1/Δ 410 nm).

The present invention will be explained practically by the following examples.

EXAMPLE 1

(Isolation of the SNA-115 productive strain)

A soil sample was collected from about 1 cm depth at Miura peninsula, Kanagawa Prefecture, Japan, The soil sample was stored in the air for 7 days at room temperature under saturated humidity, then heated at 60° C. for 1 hr. The treated soil was 10-fold diluted in sterilized water, sonicated for 1 min., and spread onto an isolation medium (glucose 5 g/L, NaCl 0.5 g/L, $K_2HPO_4$ 0.5 g/L, $MgSO_4.7H_2O$ 0.5 g/L, yeast extract 0.5 g/L, L-asparagine 0.5 g/L, soluble starch 5 g/L, $FeSO_4.7H_2O$ 0.01 g/L, agar 15 g/L, nystatin 50 mg/L, cycloheximide 50 mg/L, novobiocin 3 mg/L, rifampicin 5 mg/L and adjusted to pH 7.0). The inoculated medium was cultured at 27° C. to give grown microorganisms. The grown microorganisms were screened and identified a microorganism having above mentioned properties. The microorganism was named Microbispora sp. SNA-115 and deposited with the Agency of Industrial Science and Technology, Fermentation Research Institute as FERM BP-3890.

EXAMPLE 2

(Production of SNA-115, part 1)

A medium composed of glucose 2%, soluble starch 1%, soy bean flour 2.5%, meat extract 0.1%, dried yeast 0.4%, NaCl 0.2% and $K_2HPO_4$ 0.005% was adjusted to pH 8.4. The adjusted medium was divided 70 ml each in 500 ml volume Erlenmeyer flasks and pasteurized at 120° C. for 20 min. A loopful Microbispora sp. SNA-115 (FERM P-12094) was inoculated the medium from a slant culture and cultured at 27° C. for 10 days under shaking at 200 rpm. Two ml each of the culture was inoculated to similar medium and cultured at 27° C. for 3 days under shaking to give a pre-culture.

In a 30 L volume jar fermenter containing 18 L of similar medium, 140 ml of the pro-culture was introduced and main-cultured at 27° C. with aeration of 18 L/min. with sterilized air and stirring at 300 rpm. The culture was completed after 212 hrs. (pH 5.6) and 1.75 kg of wet cells were collected by centrifugation. The cells were extracted with acetone and the extract was lyophilized to give 34.8 g of dried extract powder. The 50% inhibitory activity ($IC_{50}$) of the powder to prolyl endopeptidase was 15.5 μg/ml. The powder was suspended in 50 ml of a mixture of chloroform and methanol (2:1) and subjected to a silica gel column chromatography (Kiesel gel 60, 70-230 mesh, E. Merck, 4×36 cm). The column was eluted with 1 L of the same solvent to remove impurities, then followed by elution with 1 L each of mixtures of chloroform and methanol (1:1) and (1:2) successively to eluate the active component (3.9 g, $IC_{50}$=2.7 μg/ml). The active fraction was dissolved in 10 ml of methanol, subjected to a column chromatography (3×73 cm) prepared of Sephadex LH-20 (Pharmacia AB, Sweden) and developed with methanol to give an active fraction (3.1 g, $IC_{50}$ 2.4 μg/ml). The fraction was dissolved in methanol, subjected to high performance liquid chromatography (HPLC) prepared of Senshu Pack ODS-5251-SS (20×250 mm) and eluted twice with a mixed elution solution of acetonitrile and 0.1% trifluoroacetic acid (TFA) (40:60). The eluate containing SNA-115 was condensed under reduced pressure and lyophilized to give 600 mg of highly pure white powder of SNA-115. SNA-115 may be obtained also in a supernatant by some changes in culture period and conditions. Fifteen L of the supernatant obtained by centrifugation was extracted 3 times with equal volume of butanol, The combined butanol extracts were condensed and lyophilized to give 46.3 g of powder. The powder was treated by the similar manner with those of cell extract to give white powder of SNA-115.

During the purification procedure, prolyl endopeptidase inhibitory activity ($IC_{50}$) was found in 0.1 mM of substrate.

EXAMPLE 3
(Production of SNA-115, Part 2)

The official strains of *Microbispora rosea* Nonomura and Ohara (IFO 14044), *Microbispora rosea* subsp. nonnitritogenes Nonomura and Ohara (IFO 14045), and *Microbispora indica* (IFO 14879) were pre- and main-cultured separately in a similar manner with that of Example 2.

The produced cells were treated with column chromatography and HPLC successively in a similar manner with that in Example 2. The patterns of three products were identical with that of SNA-115.

EXAMPLE 4
(Production of SNA-115T)

In 4.5 ml of methanol, 53.8 mg of white powder of SNA-115 obtained by the method shown in Example 2 was dissolved, 3.5 ml of 0.1M Tris-HCl buffer (pH 7.5) and 3 mg of trypsin (TPCK treated, 12,800 unit/mg, Sigma Co., Ltd.) in 1 ml of the same buffer were added and caused to react at 37° C. for 3 hrs. The reaction product was fractionated with HPLC (a reverse column prepared of SENSHU PACK®, ODS-5251-SS, 20×250 mm and a solvent system of acetonitrile:water:trifluoroacetic acid=35:64:1). The acetonitrile in the eluate was removed under reduced pressure and lyophilized to give white powder of 27.0 mg of SNA-115T.

The physicochemical properties of the white powder showed similar properties shown above.

Applicability for Industrial Use

The present invention relates to new peptides, and processes and strains for the production thereof.

The new peptides of the present invention exhibit prolyl endopeptidase inhibitory activity and are useful for the effective components of anti-amnestic agents, prevention and treatment of acquired immunodeficiency syndrome (AIDS) and anti-HIV agents. Furthermore, the peptides of the present invention can be used as biochemical and pharmacological reagents.

Deposited Microorganisms
Name of institute deposited and its location:
Agency of Industrial Science and Technology, Fermentation Research Institute.
1-1-3, Higashi, Tsukuba, Ibaraki-Prefecture, Japan
Date of deposit: Mar. 7, 1991
Deposit No.: FERM BP-3890

---

We claim:
1. Peptide SNA-115 represented by the following structural formula (I):

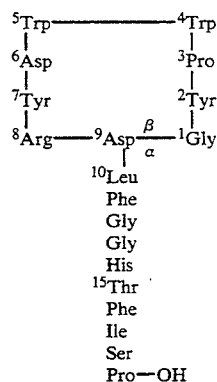

and having the following physicochemical properties:
(1) Molecular formula: $C_{113}H_{142}N_{26}O_{27}$
(2) Molar ratio of amino acid composition:

| | |
|---|---|
| Aspartic acid (or asparagine) | 2 |
| Threonine | 1 |
| Serine | 1 |
| Glycine | 3 |
| Isoleucine | 1 |
| Leucine | 1 |
| Tyrosine | 2 |
| Phenylalanine | 2 |
| Histidine | 1 |
| Arginine | 1 |
| Proline | 2 |
| Tryptophan | 2 |

(3) Rf value by thin layer chromatography: 0.36 carrier: silica gel plate F254 Art. 5715 (E. Merck), developing solvent: butanol/methanol/water (4:1:2)
(4) Prolyl endopeptidase inhibitory activity: positive, said peptide being further identified as SEQ ID NO:1:.

2. Peptide SNA-115T, represented by the following structural formula (II):

$$\text{H—Arg—Tyr—Asp—Trp—Trp—Pro—Tyr—Gly—Asp(NH}_2\text{)—}$$
$$\text{—Leu—Phe—Gly—Gly—His—Thr—Phe—Ile—Ser—Pro—OH}$$
(II)

and obtained by cleavage of the amide bond between Arg at position 8 and Asp at position 9 in the structural formula (I) of claim 1, forming free carboxyl and amino groups, said peptide being further identified as SEQ ID NO:1:.

* * * * *